(12) United States Patent  (10) Patent No.: US 7,147,469 B2
Garman  (45) Date of Patent: Dec. 12, 2006

(54) ENDODONTIC INSTRUMENT

(75) Inventor: Gary T. Garman, La Verne, CA (US)

(73) Assignee: Ormco Corporation, Orange, CA (US)

( * ) Notice: Subject to any disclaimer, the term of this patent is extended or adjusted under 35 U.S.C. 154(b) by 77 days.

(21) Appl. No.: 10/229,421

(22) Filed: Aug. 28, 2002

(65) Prior Publication Data

US 2004/0043357 A1    Mar. 4, 2004

(51) Int. Cl.
*A61C 5/02*    (2006.01)
(52) U.S. Cl. .................................... 433/102
(58) Field of Classification Search .............. 433/102, 433/224, 165, 166, 144
See application file for complete search history.

(56) References Cited

U.S. PATENT DOCUMENTS

| | | | | |
|---|---|---|---|---|
| 4,634,378 | A | * | 1/1987 | Leonard ...................... 433/102 |
| 5,816,807 | A | * | 10/1998 | Matsutani et al. .......... 433/165 |
| 5,882,198 | A | | 3/1999 | Taylor et al. ................ 433/102 |
| 5,902,106 | A | | 5/1999 | McSpadden ................ 433/102 |
| 5,938,440 | A | | 8/1999 | McSpadden ................ 433/102 |
| 5,975,899 | A | | 11/1999 | Badoz et al. ................ 433/102 |
| 5,980,250 | A | | 11/1999 | McSpadden ................ 433/102 |
| 6,179,616 | B1 | * | 1/2001 | Danger ....................... 433/165 |
| 6,299,445 | B1 | | 10/2001 | Garman ...................... 433/102 |

FOREIGN PATENT DOCUMENTS

EP      1 108 395 A2    6/2001

OTHER PUBLICATIONS

SybronEndo, $K^3 = \sqrt{Endo}$™, Product Brochure, Ref. 077-3038 Rev. A, 2 pp., 2001.
Analytic Endodontics, *Gradually Revolutionary, The Quantec System*, Product Brochure, Part No. 077-3051 Rev. C, 4 pp., date unknown.
Dentsply Maillefer Instruments, *ProTaper™, Progressively Tapered Nickel Titanium Rotary Files*, Product Brochure, 6 pp., date unknown.
Dentsply Maillefer Instruments, *ProFile®*, Product brochure, 19 pp., no translation, date unknown.
John D. West, DDS, MSD, *Introduction of a New Rotary Endodontic System: Progressively Tapering Files*, Dentistry Today, pp. 50-57, May 2001.
Serene et al., *Nickel-Titanium Instruments—Applications in Endodontics*, Ishiyaku EuroAmerica, Inc., 107 pp., 1995.

* cited by examiner

*Primary Examiner*—Melba N. Bumgarner
(74) *Attorney, Agent, or Firm*—Wood Herron & Evans, LLP

(57) ABSTRACT

A non-landed endodontic instrument has flutes formed along a working length of the instrument shaft. The flutes define cutting edges for shaping a root canal of a tooth. The cutting edges lie at a major diameter of the shaft and peripheral flute surfaces behind the cutting edges extend along decreasing radial distances from the center of the shaft, in a direction opposite the cutting direction of the instrument.

2 Claims, 2 Drawing Sheets

ENDODONTIC INSTRUMENT

FIELD OF THE INVENTION

This invention relates generally to the field of endodontics, and more particularly to instruments and methods for extirpating and enlarging a root canal.

BACKGROUND OF THE INVENTION

In the field of endodontics, one of the most important and delicate procedures is that of cleaning or extirpating a root canal to provide a properly dimensioned cavity while essentially maintaining the central axis of the canal. This step is important in order to enable complete filling of the canal without any voids and in a manner which prevents the entrapment of noxious tissue in the canal as the canal is being filled.

In cleaning and enlarging the root canal, instruments called files, or reamers, are used. Commonly, both files and reamers have flutes which spiral along a portion of the instrument length and define cutting edges used to shape the root canals. The classification of an instrument as a file or a reamer depends upon the pitch of the flutes. A instrument having a greater pitch enables the instrument to cut better in a rotary mode, hence the instrument is a reamer. An instrument having a lesser pitch enables the instrument to cut better in the reciprocating mode, hence a file. During a cleaning and shaping operation performed with such a file or reamer, the instrument is normally rotated and moved into and out of the root canal along the longitudinal axis of the instrument.

Root canal files are available in various cross-sectional geometries and typically have two, three, four or even more cutting edges. Files can be classified as either landed or non-landed files depending on the geometry of the cutting edge. Non-landed files generally have a sharp cutting edge which extends from a central axis of the file as depicted in FIG. 2 which illustrates a cross-section of a non-landed file 110 having three flutes 112 and three cutting edges 114, 114a and wherein the spiral configuration has been removed for clarity. The sharp cutting edge 114 is relatively weak and therefore may be distorted or folded back upon itself in a direction opposite the cutting direction CD if excessive forces are applied while in use, as illustrated by cutting edge 114a. Such distortion of the cutting edge 114a severely lessens its effectiveness or makes the instrument 110 unusable.

Landed files were developed to address the strength problems of non-landed files. Referring to FIG. 3, the cutting edges 122 of landed files 120 do not terminate in a sharp point. Instead, they are reinforced with a thick section of material directly behind the cutting edge 122, creating a lobe-like protrusion with the cutting edge 122 at the leading edge of a land surface 124. While landed files exhibit increased strength at the cutting edge, they also significantly increase the friction between the file and the tooth. This increased friction generates undesirable heat in the canal and increases the stress on the file, which can lead to failure and breakage of the instrument. Indeed, one of the problems with traditional endodontic instruments used for extirpating and filing root canals is that the torsional limitations of the instrument are often exceeded, resulting in breakage of the instrument.

In an attempt to address the increased friction of landed files of the type depicted in FIG. 3, files with reduced land surface areas have been developed, as depicted in FIG. 4. This modified-land file 130 has three flutes 132 defining three cutting edges 134 at the leading edge of a reduced surface area land 136. The remaining portion 138 of the land 136 is stepped down to reduce the amount of surface area in contact with the tooth. While these modified-land files provide improved strength, compared to non-landed files, they still generate undesired friction within the canal.

There is thus a need for an endodontic instrument which exhibits improved strength at the cutting edge and overcomes problems of prior art endodontic instruments, such as those described above.

SUMMARY OF THE INVENTION

The present invention provides an endodontic instrument for use in shaping a root canal in which the cutting edges have been optimized for strength while minimizing the amount of friction generated within the canal. The instrument has an elongate shaft with a working length along a portion of the shaft. At least one non-landed flute is formed on the outer surface of the working length and defines a cutting edge at a radial distance from the axial center of the shaft. Behind the cutting edge, the outer surface of the shaft decreases in radial distance from the axial center of the shaft to form a peripheral flute surface that does not make contact with the interior surface of the root canal of the tooth. Advantageously, the peripheral flute surface provides strength to the cutting edge but does not create unwanted friction within the canal.

In an exemplary embodiment, the boundary of the peripheral flute surface behind the cutting edge is along a line of force defined by the resultant vector of the tangential and radial forces at the cutting edge. This configuration maximizes the effectiveness of the peripheral flute surface in strengthening the cutting edge because any material radially outward of the boundary does not contribute to strengthening the cutting edge.

In accordance with the invention, a method of shaping the root canal of a tooth includes the steps of a) providing an endodontic instrument with an elongate shaft having an axial center and a working length along at least a portion of the shaft, the working length including an outer surface, at least one non-landed flute formed on the outer surface and having a cutting edge at a first radial distance from the axial center and a peripheral flute surface extending therefrom in a direction opposite the direction of cutting rotation, the peripheral flute surface having its maximum radial distance from the axial center at the cutting edge and decreasing from the maximum distance in a direction opposite the direction of cutting rotation, to terminate in a trailing edge, b) inserting the endodontic instrument into the root canal, and c) manipulating the endodontic instrument to remove portions of the tooth.

The features and objectives of the present invention will become more readily apparent from the following Detailed Description taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION

Figure 1:
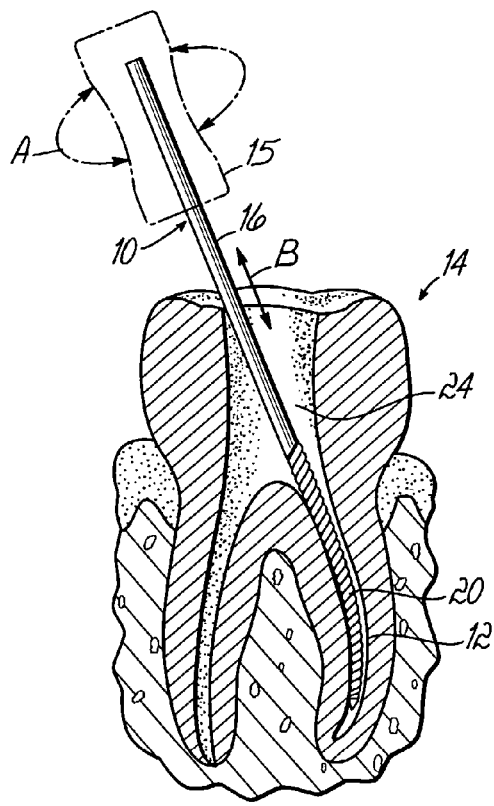
FIG. 1 is a cross-sectional view of a tooth illustrating a canal being shaped with a file.
Figure 1A:
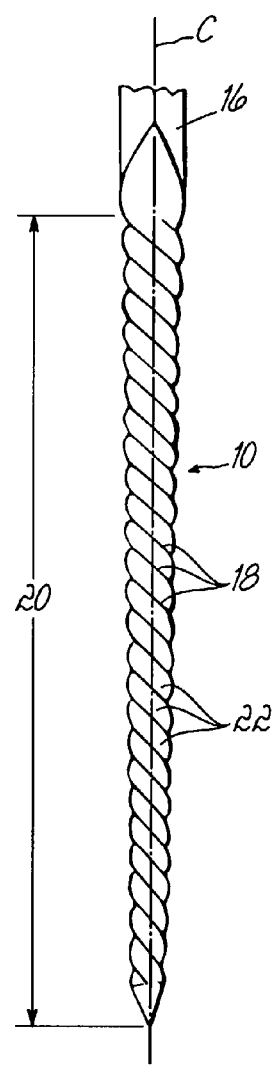
FIG. 1A is detail view of the shaft of a file.
Figure 2:
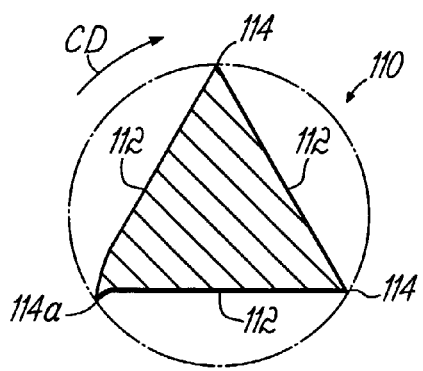
FIG. 2 is a cross-sectional view of a prior art non-landed file.
Figure 3:
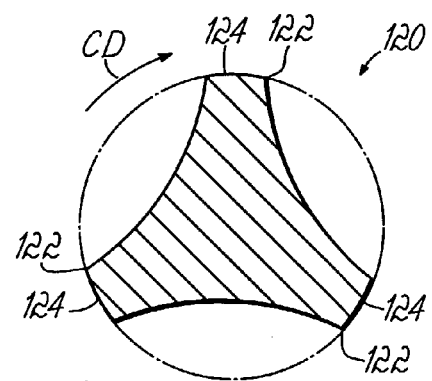
FIG. 3 is a cross-sectional view of a prior art landed file.
Figure 4:
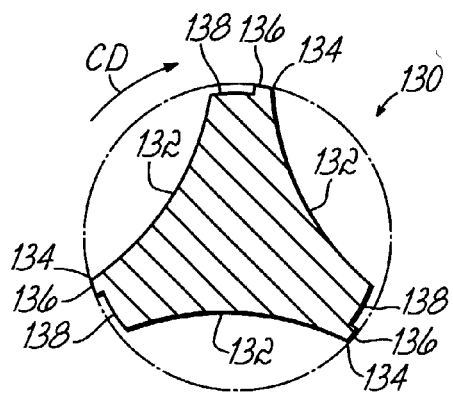
FIG. 4 is a cross-sectional view of a prior art modified-land file.

Referring to FIGS. 1–2, there is shown an exemplary endodontic instrument 10 of the present invention being used to shape a root canal 12 of a tooth 14. The endodontic instrument 10 includes a handle 15 for manual gripping by, for example, an endodontist and an elongate shaft 16 having cutting edges 18 for shaping the tooth 14. A portion of the shaft 16 comprises a working length 20 having helical flutes 22 which form the cutting edges 18 of the endodontic instrument 10. In use, the working length 20 of the instrument 10 is inserted into a root canal 12 of a tooth 14 through an upper interior portion 24 of the tooth 14 which has been initially opened using another instrument, such as a drill (not shown). Although files and reamers are typically manipulated manually, the instrument 10 of the present invention may be adapted for use with power operated equipment as well. In a conventional manner, the instrument 10 may be rotated in the direction of arrows A and/or reciprocated in the direction of arrow B to clean out and enlarge the root canal 12.

Figure 5:
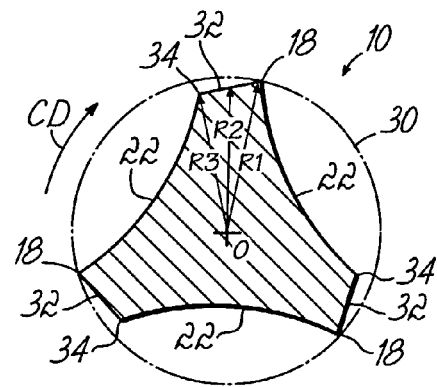
FIG. 5 is a cross-sectional view of an exemplary file of the present invention.

Referring to FIG. 5, a cross-sectional view of a portion of the working length 20 of the instrument 10 is shown, wherein the helical configuration has been eliminated for clarity. In the exemplary embodiment shown, the instrument 10 has three cutting edges 18 defined by three flutes 22 and three peripheral flute surfaces 32 that extend from the cutting edges 18 to trailing edges 34, in directions opposite the cutting direction CD. While three cutting edges 18 are shown in the exemplary embodiment, it will be understood that the instrument 10 may have a lesser number or a greater number of cutting edges 18, as may be desired.

The cutting edges 18, which constitute the leading edges when the instrument 10 is rotated to produce cutting action, are located radially outward from the axial center O of the instrument 10 a distance $R_1$ which extends to the major diameter 30. Behind the cutting edges 18, that is, in a direction from the leading edge to the trailing edge 34, the peripheral flute surfaces 32 are located radially outward from the axial center O distances that are less than the radial distances $R_1$ of the cutting edges 18. Advantageously, this configuration ensures that the peripheral flute surfaces 32 will not contact the interior surface of tooth 14 in the root canal 12. In the exemplary embodiment shown in FIG. 5, peripheral flute surfaces 32 lie at decreasing radial dimensions $R_1, R_2, R_3$ from the axial center O of the instrument 10, in a direction opposite the cutting direction CD, from the cutting edges 18 to the trailing edges 34. In another exemplary embodiment, the boundaries of the peripheral flute surfaces 32 are determined by the lines of force exerted by the cutting edges 18 on a tooth 14, as described more fully below.

Figure 6:
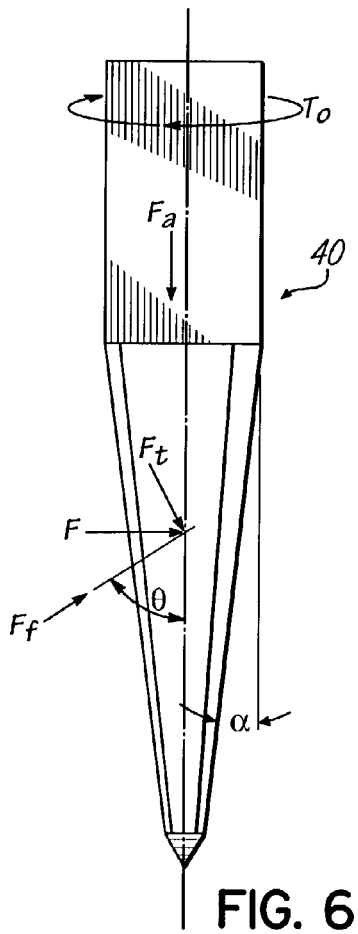
FIG. 6 is a schematic of a file shaft illustrating forces acting on a file.
Figure 7:
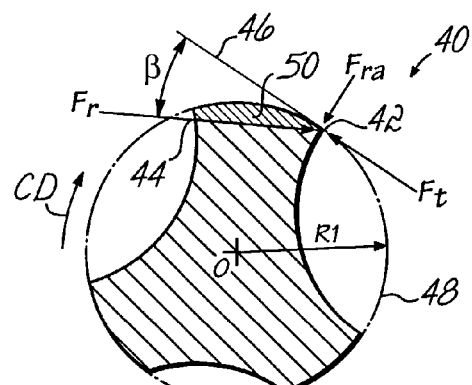
FIGS. 7–8 are cross-sectional views of a landed file illustrating forces acting on a file.

FIGS. 6 and 7, illustrate the forces on an endodontic instrument 40 during the shaping of a root canal 12. As the instrument 40 is inserted into a root canal 12 and manipulated to enlarge the canal by cutting chips from the tooth with the cutting edge 42, the endodontist will apply an axial force $F_a$ and a torque $T_o$ to the instrument 40. The torque $T_o$ applies by the endodontist will be a function of the file type and geometry and the applied axial force $F_a$. In practice, measured values of axial force $F_a$ have ranged from approximately 20 grams to over 1000 grams. At the cutting edge 42, the instrument 40 will experience a compressive force $F_{ra}$ related to the compression of the instrument 40 against the outer walls of the canal and a tangential cutting force $F_t$ tangent to the major diameter 48 at the cutting edge 42. The tangential cutting force $F_t$ is one component of the tangential cutting and frictional force F, and is related to the torque $T_o$ and to the geometry of the cutting instrument 40. $F_f$ is the tangential frictional force, which has no effect on the strength of the cutting edge 42.

Figure 8:
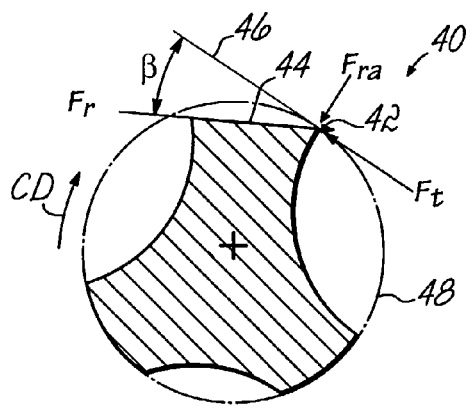

The radial and tangential forces $F_{ra}$, $F_t$ may be resolved into a resultant force $F_r$ which must be exerted by the instrument 40 at the cutting edge 42 in order to cut a chip from the root canal 12. The resultant force $F_r$ will be applied along a line of action 44 that forms an angle β with a tangent line 46 to the major diameter 48 at the cutting edge 42. The angle β can be determined from the formula:

$$\beta = \arctan\left[\frac{R_1 F_a \tan\alpha}{T_o \cos\theta}\right]$$

where:
   $R_1$=radius at the cutting edge
   $F_a$=axial force along instrument
   α=file side taper angle
   $T_o$=torque applied to file
   θ=file helix angle Because the resultant force $F_r$ applied by the instrument 40 at the cutting edge 18 acts along a line 44 which forms an angle β with a tangent 46 to the major diameter 48 at cutting edge 18, it will be recognized that material 50 of the cutting instrument 40 which lies radially outward of the line of action 44 of the resultant force $F_r$ does not increase the strength of the instrument 40 at the cutting edge 42. Accordingly, this material 50 may be removed without effecting the strength of the instrument 40 at the cutting edge 42, as depicted in FIG. 8. Thus, in an exemplary embodiment, an instrument 10 of the present invention may be configured such that peripheral flute surfaces 32 are formed to lie along lines of action corresponding to the resultant forces $F_r$ and located approximately at angles β to lines tangent to the major diameter 30 at cutting edges 18, as defined by the formula above. The angle β may be constant along the working length 20 of a given instrument, or it may vary along the working length 20, as may be desired.

While the present invention has been illustrated by the description of the various embodiments thereof, and while the embodiments have been described in considerable detail, it is not intended to restrict or in any way limit the scope of the appended claims to such detail. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of Applicant's general inventive concept.

What is claimed is:

1. A tapered endodontic instrument, comprising:
an elongate shaft having an axial center and a working length along at least a portion of said shaft, said working length including an outer surface;
at least one non-landed flute formed on said outer surface and having a cutting edge at a first radial distance from said axial center; and
at least one peripheral flute surface formed on said outer surface and extending from said cutting edge in a direction opposite a cutting direction of the instrument, said peripheral flute surface located from said axial center a radial distance less than said first radial distance;
wherein said peripheral flute surface extends along a line of force defined by the resultant vector of tangential and radial forces at said cutting edge when the instrument is used to cut dentin of a tooth.

2. A method of shaping the root canal of a tooth, comprising:
providing a tapered endodontic instrument having:
an elongate shaft having an axial center and a working length along at least a portion of the shaft, the working length including an outer surface,
at least one non-landed flute formed on the outer surface and having a cutting edge at a first radial distance from the axial center, and
at least one peripheral flute surface formed on the outer surface and extending from the cutting edge in a direction opposite a cutting direction of the instrument, the peripheral flute surface located from the axial center a radial distance less than the first radial distance, wherein the peripheral flute surface extends along a line of force defined by the resultant vector of tangential and radial forces at the cutting edge when the instrument is used to cut dentin of a tooth;
inserting the endodontic instrument into the root canal; and
manipulating the endodontic instrument to remove portions of the tooth.

* * * * *